United States Patent [19]
Wang et al.

[11] Patent Number: 5,618,996
[45] Date of Patent: Apr. 8, 1997

[54] METAL SAMPLING METHOD AND SYSTEM FOR NON-HYDROLYZABLE GASES

[75] Inventors: Hwa-Chi Wang, Naperville; Richard J. Udischas, Chicago, both of Ill.

[73] Assignee: American Air Liquide Inc., Houston, Tex.

[21] Appl. No.: 609,836

[22] Filed: Mar. 1, 1996

[51] Int. Cl.$^6$ .................................................. G01N 1/22
[52] U.S. Cl. ............................. 73/863.61; 73/863.23; 73/863.12
[58] Field of Search ..................... 73/863.12, 863.61, 73/863.23

[56] References Cited

U.S. PATENT DOCUMENTS

| | | | |
|---|---|---|---|
| 2,322,018 | 6/1943 | Huber | 73/863.61 X |
| 3,429,186 | 2/1969 | Price et al. | 73/863.61 |
| 4,004,882 | 1/1977 | Byrne et al. | 73/863.12 X |
| 4,317,379 | 3/1982 | Oberländer et al. | 73/863.12 |
| 4,979,403 | 12/1990 | Pike | 73/863.23 X |
| 5,142,143 | 8/1992 | Fite et al. | 73/863.12 X |

Primary Examiner—Thomas P. Noland
Attorney, Agent, or Firm—Burns, Doane, Swecker & Mathis, L.L.P.

[57] ABSTRACT

Provided is a portable system useful for sampling both particulate and vapor phase metallic impurities from gases that cannot by hydrolyzed. The system comprises valves for introducing and controlling the exhaust of the gas to be sampled from the system. The metallic impurities are entrapped on filters, with one filter being operated at ambient temperature to remove particulate metallic impurities, and with another filter being operated at a temperature below ambient in order to remove vapor phase metallic impurities. In operating the system, the system is first back-filled to create a pressure equilibrium across the valve which introduces the gas to the first filter means. The flow of gas through the entire sampling system is controlled by means of a critical orifice located between the filters and the valve for controlling exhaust of the gas from the system. The entire system is portable and allows for transport of the system with its filters to a laboratory in order to permit the most sophisticated and effective analysis of the metallic impurities in the filters under controlled laboratory conditions.

18 Claims, 1 Drawing Sheet

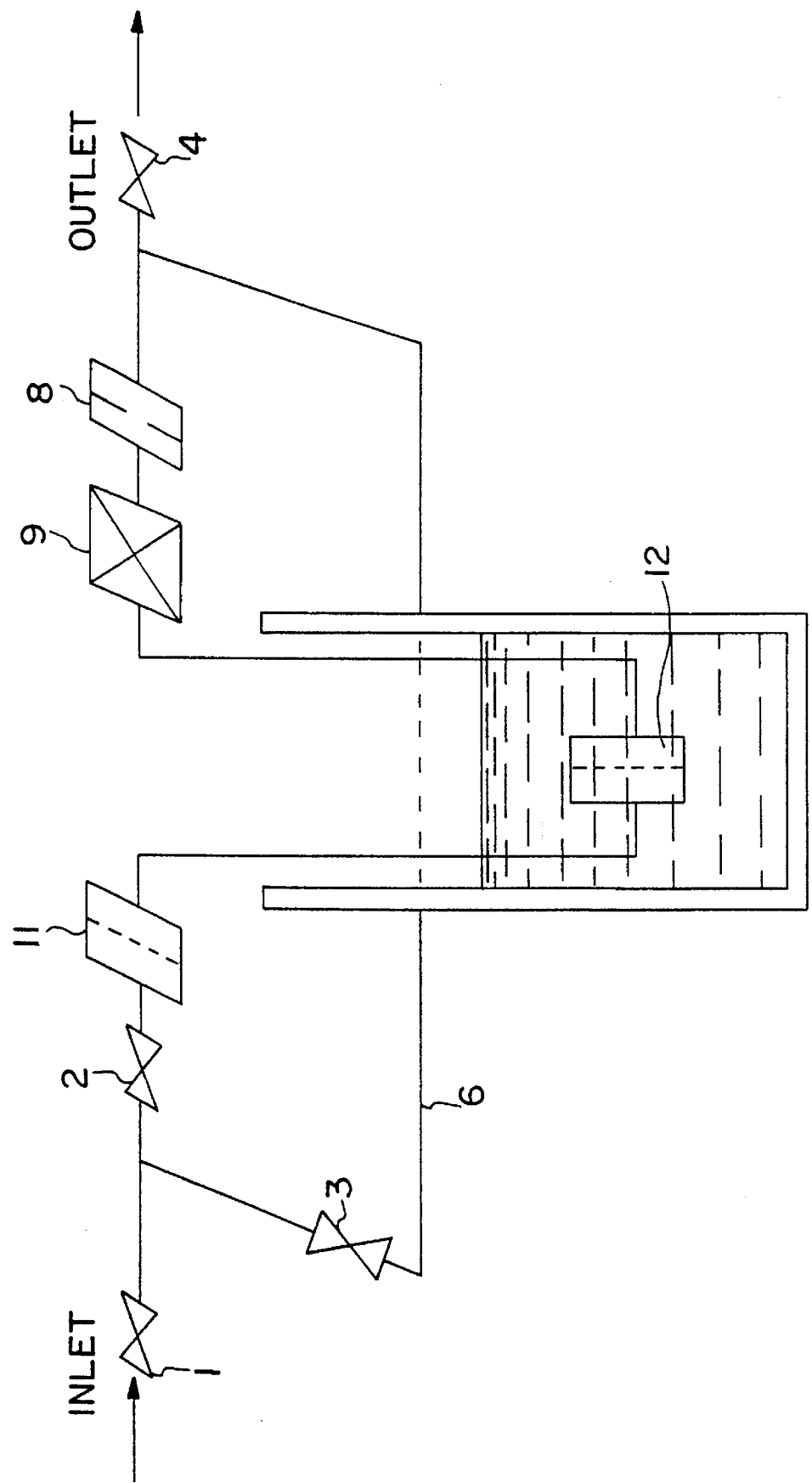

METAL SAMPLING METHOD AND SYSTEM FOR NON-HYDROLYZABLE GASES

BACKGROUND OF THE INVENTION

1. Field of the Invention

The present invention relates to a method and a system for sampling a gas for both particulate and vapor phase metal impurities. In particular, the system of the present invention is very portable in that it can be easily removed from the site of the gas being sampled and returned to a laboratory for an accurate analysis of the metal impurities trapped in the filters of the system.

2. Brief Description of the Prior Art

A very important and crucial aspect in semi-conductor manufacturing is the constant control of metallic impurities in process gases. Generally, the impurities are present due to corrosion, shedding from values and the like. In order to reduce the metallic impurities in the gases prior to their reaching the semiconductor manufacturing process, the gases flowing through the system must be sampled. Analysis of the gases can indicate whether metallic impurities, being introduced from outside the system or being created inside the system, are contaminating the manufacturing process. The level of detection for metallic impurities in semiconductor manufacture processes must reach the parts per trillion level, and therefore requires very sophisticated equipment for analysis and detection.

Methods for sampling gases in order to detect metallic impurities have applications well beyond the semi-conductor manufacturing industry. In most of the methods used, the gases are hydrolyzable, i.e., dissolvable in water, and therefore hydrolysis is commonly used for sampling the metals in the gases. However, gases such as nitrogen, $SiH_4$, and $CF_4$, some of which are commonly used in semi-conductor manufacturing processes, are not hydrolyzable. Therefore, in order to sample the gases and detect metal impurities in the gases, a filtering system must be used.

To render such a filtering system most useful for the industry, it must be very efficient and effective for measuring and detecting metallic impurities to the parts per trillion level. Efficiency in such detection often requires the most sophisticated of analysis equipment, and therefore it would also be most desirable if such a filtering system were portable so that it can be easily transported to a laboratory where access to the necessary analysis equipment can be had.

Accordingly, it is an object of the present invention to provide a sampling system and method for using such a system to sample non hydrolyzable gases and analyze the gases for metal impurities.

It is another object of the present invention to provide methods and systems to sample non-hydrolyzable gases for both particulate and vapor phase metallic impurities in an effective and efficient manner.

It is yet another object of the present invention to provide a portable system for sampling non-hydrolyzable gases for the ultimate detection of metallic impurities so that the sophisticated analysis equipment typically required can be easily used at an off-site laboratory.

These and other objects of the present invention will become apparent upon a review of the following specification, the FIGURE of the Drawing, and the claims appended hereto.

SUMMARY OF THE INVENTION

In accordance with the invention, a portable system useful for sampling both particulate and vapor phase metallic impurities from gases that cannot be hydrolyzed is presented, as well as a method of using same.

The system preferably comprises a first valve means for introducing the gas to be sampled to the system. A first filter means is located downstream of the first valve means, which first filter means is used to remove particulate metallic impurities, preferably at ambient temperature (about 20°–25° C.). A second filter means in series with the first filter means is used to remove vapor phase metallic impurities. This second filter means is preferably operated at a temperature below ambient temperature but above the freezing point of the gas being sampled. A third filter means is also located downstream of the first and second filter means for removing substantially any impurities in the gas. The system further comprises a second valve means downstream from the first valve means but upstream from the first filter means. Third and fourth valve means are also included in the system, with the fourth valve means being located downstream of all of the filter means and is used for controlling the exhaust of the gas from the system. The third valve means allows for the gas to be conducted in parallel with respect to the filters in the system to the fourth valve means. A critical orifice is also located between the third filter means and the fourth valve means for back-filling the gas being sampled through the filters in the system until there is a pressure equilibrium across the second valve means for reasons that will become apparent.

The system of the invention is most preferably portable and can be transported quite easily, generally using a system pressure of less than 20 psig. Due to the portability of the inventive system, the filters can be transported to a laboratory which can analyze the filters for particulate and vapor phase metallic impurities.

A preferred method of using the system comprises first opening the first and third valve means, while keeping the second and fourth valve means closed. This allows the gas being sampled to back-fill through the critical orifice and the third filter means, which is an absolute filter to ensure that the system is filled first with only clean (i.e., metal impurity-free) gas. This back-filling allows a pressure equilibrium to be established across the second valve means. This pressure equilibrium is important as it substantially reduces, and preferably prevents particle shedding from the second valve when it is opened. After the back-filling is complete, the third valve means is closed, and the second and fourth valve means are opened to allow sampling to begin. Metallic impurities are trapped in the first and second filter means. After the necessary sampling duration, the first and fourth valve means are closed in order to close the entire system. The system can then be disconnected from the customer's process and sent to a laboratory for analysis of the filters.

BRIEF DESCRIPTION OF THE FIGURE OF THE DRAWING

The FIGURE of the drawing is a schematic representation (reduced in scale) of a system in accordance with the present invention, and is illustrative only.

DESCRIPTION OF PREFERRED EMBODIMENTS

The system of the present invention is preferably portable and allows for the efficient and effective sampling of gases which are non-hydrolyzable in order to determine the extent of any metallic impurities in said gases. As used herein, portable means the system can be disconnected from the gas supply being sampled and sent to the location of the analysis equipment. The location of analysis equipment may be removed from the sampling site, or on-site. The portability of the present system allows its use in many different locations, yet further allows analysis of the gases sampled to be conducted with the most sophisticated equipment possible in the most efficient and effective manner.

The system and the method used in sampling gases with the system will be described in more detail in reference to the FIGURE of the drawing. In the FIGURE, a first valve means 1 is generally connected to the system from which the gas is to be sampled. The connection may be any type of connection means commonly used in gas systems. First valve means 1 allows the gas to be sampled to be introduced into the sampling system illustrated. A fourth valve means 4 of the sampling system controls the exhaust of the gas from the system.

A second valve means 2 of the system is located downstream from first valve means 1 but upstream from a first filter 11. First filter means 11 is used to remove particulate impurities at ambient temperature. The filter is generally and preferably a membrane filter and has an effective pore size of about 0.2 micrometer. Membrane filter 11 can be any appropriate membrane filter, but is most preferably a teflon membrane filter, such as those commercially available. Ceramic filters may also be employed. In series with filter means 11 is filter means 12. Filter means 12 is generally composed of the same media as filter means 11, but is maintained at a lower temperature than ambient temperature, and at a temperature greater than the freezing point of the gas being sampled. This lower than ambient temperature is utilized in order to have vaporous metal impurities nucleate or condense onto the membrane filter. In general, the temperature of the filter 12 is maintained in the range of from $-80°$ C. to about $0°$ C. The use of dry ice and a methanol liquid bath will maintain the filter at about $-60°$ C. Other combinations of coolants and temperature baths can be used in order to vary the temperature of second filter means 12. In a preferred embodiment of using a carbon dioxide ice/methanol liquid bath to maintain the temperature of filter 12 at $-60°$ C., the methanol liquid functions primarily to increase the contact area of the bath with the filter to ensure uniform temperature.

An important aspect of the present system is that it allows back-filling of the system with clean gas to create an equal pressure on both sides of second valve means 2. This pressure equilibrium allows one to avoid particle shedding when valve means 2 is opened. Shedding is basically a mechanical friction and corrosion problem. It involves the release of particles from internal wetted surfaces, i.e., anything the gas comes into contact with in the system. The release of the particles is caused generally by pressure pulses or flow pulses, which provide the energy to pull the particle into the gas.

The back-filling is accomplished by use of a conduit 6 which is in parallel flow arrangement with the filters in the system. Gas flowing through conduit 6 is controlled by a third valve means 3 in the system. When valve means 3 is open, gas will flow parallel to the filters in the system directly to valve means 4, where it will be exhausted from the system when valve means 4 is open. However, when valve means 4 is closed, the gas conducted via means of conduit 6 will back-fill through the filters in the system. The backfilling takes place through an orifice 8 and absolute filter 9. Orifice 8 is preferably a critical orifice, and is used to control the flow of gas through the system. The critical orifice can be stainless steel disk, for example, with one hole which is sized to correspond to the pressure one plans on working with in the system. The hole is sized appropriately based on the desired pressure in order to give the desired flow rate. The orifice can be made out of sapphire or other suitable materials besides stainless steel.

The absolute filter 9 is generally a ceramic or metal filter which removes substantially all impurities which may be contained in the gas to be sampled. The filter is preferably a ceramic filter which has a rating of 0.01 micrometer or lower. The use of this filter ensures that clean gas is back-filled through the system.

The amount of time that back-filling takes place generally ranges from about one–two minutes. Of course, critical orifice 8 controls the flow, and therefore the choice of the critical orifice size can control the amount of time it would take to back-fill the entire system. In general, however, about two minutes is all that is necessary to slowly fill the system and create the same pressure on both sides of second valve means 2. Once the system has been back-filled, sampling of the gas through the system can take place, with particulate impurities being entrapped in filter means 11 and vapor phase metallic impurities being entrapped in filter means 12.

Once sampling has been completed, the system is closed, generally by closing valve means 1 and 4. The closed system is then disconnected from the customer's facility and, due to its portability, then can be simply transported from the system from which the sampled gas has been taken to the analysis location. For example, the portable system is preferably transported to a laboratory where analysis of the filters can take place in order to indicate the extent of metal impurities in the sampled gas. Generally, an acid solution, preferably a mixture of nitric acid and hydrochloric acid, is used to remove the metals from filters 11 and 12. This acid solution containing the metal impurities is then injected into an instrument such as ICPMS (Inductively Coupled Plasma Mass Spectrometer) or a GFAA (Graphite Furnace Atomic Absorption) instrument. Both of these types of instruments are extremely sophisticated, but the operation of the instruments is known to skilled artisans and the instruments are commercially available, for example from Perkin-Elmer.

Of particular utility of the present portable system is the ability to entrap vapor metal impurities. Such impurities can often comprise aluminum, copper, zinc, iron, chromium, cobalt, manganese or magnesium, as well as molybdenum. The aluminum can often be generated from aluminum oxide used in adsorbents. Even small quantities in parts per trillion of such metals can do damage in very sensitive processes such as semi-conductor manufacturing processes. Thus, detection of such metals, particularly in the vapor phase, would allow a re-evaluation of the manufacturing process, and would permit one to detect leaks and/or sources of the impurities more conveniently by moving the sample system from sample port to sample port.

A calculation of the concentration of metals in the gas can be made by continuously monitoring the pressure across first filter means 11 in the system. The measurement of the pressure can be monitored by a transducer on a continuous basis with the data being fed into a computer. Orifice 8 and its size together with the pressure information can be used to calculate the mass of gas sampled. The metals analysis can provide the mass of the metal. Therefore, using the mass of the gas and metal allows one to calculate the concentration of the metals in the gas sampled. It is often important to continuously monitor the pressure across the first filter means 11 because the pressure in many plants or systems can vary quite a bit over time. Thus, continuous monitoring of the pressure is often necessary for an accurate calculation.

In referring to the FIGURE of the drawing once again, a method of utilizing the system for sampling the gas and detecting metallic impurities therein will be described in more detail. First, the system is connected to the desired sample point, with all valves of the system closed. Prior to beginning sampling, valves 1 and 3 are opened so that pressure can be equalized on both sides of valve means 2. In opening valves 1 and 3, the gas is allowed into the system and the sampled gas back-fills the system through the various filters. The back-fill of the gas goes through orifice 8 and absolute filter 9, as well as filters 12 and 11. After pressure has been equalized on both sides of valve means 2, which generally takes about one to three minutes, valve means 3 is closed, and valve means 2 and 4 are opened. Preferably, valve means 4 is opened slowly in order to ensure there are no pressure fluctuations throughout the system. Once the necessary sampling has been completed, valve means 1 and 4 are closed in order to close down the system. The sampling system can then be removed and is generally transported at a pressure of less than about 20 psig (238.4 KPa) to an off-site laboratory for analysis.

While the invention has been described with preferred embodiments, it is to be understood that variations and modifications may be resorted to as will be apparent to those skilled in the art. Such variation and modifications are to be considered within the purview and the scope of the claims appended hereto.

What is claimed is:

1. A portable system useful for sampling both particulate and vapor phase metallic impurities from gases that cannot be hydrolyzed, which system comprises:

a sample conduit and a parallel conduit, said parallel conduit connected to said sample conduit at first and second locations, the second location downstream of the first location;

first valve means upstream of said first location for introducing gas into said sample and parallel conduits and fourth valve means downstream of the second location, for controlling the exhaust of a gas from the sampling system;

first and second filter means in said sample conduit in series to remove particulate and vapor phase metallic impurities, respectfully, from the gas being sampled;

second valve means upstream of the first and second filter means but downstream of the first valve means and first location, said second valve means for introducing the gas into the system;

third valve means in said parallel conduit, for allowing gas to be conducted in parallel with respect to the first and second filter means of the system from the first valve means to the fourth valve means; and an orifice located in the sample conduit downstream of the first and second filters of the system, but upstream of the second location, through which orifice back-filling of the gas through the first and second filters in the system is permitted until pressure on both sides of the second valve means is equalized.

2. The system of claim 1, wherein the second filter means is maintained at a temperature in the range of from about −80° C. to 0° C.

3. The system of claim 2, wherein the second filter means is maintained at said temperature by use of a dry ice/methanol liquid bath.

4. The system of claim 1, wherein the first and second filter means are membrane filters, and the third filter means is a ceramic filter.

5. The system of claim 4, wherein the membrane filters of the first and second filter means are teflon membrane filters.

6. The system of claim 5, wherein the teflon membrane filters have a pore size of 0.2 micrometer.

7. The system of claim 4, wherein the ceramic filter is rated at 0.01 micrometer or less.

8. The system of claim 1, wherein all valve means are stainless steel high-pressure diaphragm valves.

9. A method for sampling a gas for both particulate and vapor phase metallic impurities using the apparatus of claim 1, which comprises first opening of the first and third valve means while keeping the second and fourth valve means of the system closed, thereby allowing the gas to back-fill through the orifice and the filter means of the system in order to create a pressure equilibrium on both sides of the second valve means, closing the third valve once the back-filling is complete and opening the second and fourth valve means to allow sampling to occur by means of trapping any metallic impurities in the first and second filter means, and closing the first and fourth valve means to complete sampling.

10. The method of claim 9, wherein the method further comprises removing the entire supply system from the system to which it is connected and from which the gas has been sampled, and transporting the sampling system to a laboratory for analysis of the metal content of the first and second filters.

11. The method of claim 10, wherein the analysis of the first and second filters is conducted using an Inductively Coupled Plasma Mass Spectrometer or a Graphite Furnace Atomic Absorption instrument.

12. The method of claim 10, wherein the pressure of the system is less than 20 psig.

13. The method of claim 9, wherein the pressure across the first filter means is monitored continuously.

14. The method of claim 9, wherein the second filter means is operated at a temperature in the range of from −80° C. to 0° C.

15. The method of claim 14, wherein a dry ice/methanol liquid bath is used to maintain the temperature of the second filter means.

16. The method of claim 9, wherein the first and second filter means are membrane filters and the third filter means is a ceramic filter.

17. The method of claim 9, wherein all of the valve means are stainless steel high-pressure diaphragm valves.

18. A portable system useful for sampling both particulate and vapor phase metallic impurities from gases that cannot be hydrolyzed, which system comprises a first valve means for introducing said gas to the system, a first filter means located downstream of said first valve means for removing particulate metallic impurities at ambient temperature, a second filter means in series with the first filter means for removing vapor phase metallic impurities, which second filter means is operated at a temperature below ambient temperature but above the freezing point of the gas being sampled, a third filter means downstream of the first and second filter means for removing substantially any impurity in the gas, a second valve means downstream from the first valve means but upstream from said first filter means, third and fourth valve means, with the fourth valve means located downstream from all of the filter means, with the fourth valve means controlling the exhaust of gas from the system, and the third valve means allowing gas to be conducted in parallel with respect to the filters in the system to the fourth valve means, and a critical orifice located between the third filter means and the fourth valve means for back-filling said gas through the filters in the system until there is a pressure equilibrium across said second valve means.

* * * * *